United States Patent [19]
Petit et al.

[11] Patent Number: 5,837,669
[45] Date of Patent: Nov. 17, 1998

[54] PHOSPHORIC ESTERS OF ALKYL OR ACYL DIANHYDRO-1,4:3,6-D-GLUCITOL, PREPARATION PROCESS AND USES THEREOF

[75] Inventors: Serge Petit, Cusy; Stephane Fouquay, Mont-Saint-Aignan; Daniel Bernard, Courbevoie, all of France

[73] Assignee: Ceca S.A., France

[21] Appl. No.: 824,728

[22] Filed: Mar. 26, 1997

[51] Int. Cl.[6] .............................. C11D 1/34; C07H 11/04
[52] U.S. Cl. .......................................... 510/467; 549/220
[58] Field of Search ............................ 549/220; 510/467, 510/515, 470

[56] References Cited

PUBLICATIONS

D. Abenhaim et al., "Selective alkylations of 1,4:3,6–dianhydro–D–glucitol (isosorbide)," vol. 261, No. 2, 1994, pp. 255–266.
W. Jasinski et al., "Preparation of Phosphate Monoesters of 1,4:3,6–dianhydro–D–glucitol and Higher Fatty Acids," Chemical Abstracts, Abstract No. 146767h, vol. 79, No. 25, Dec. 24, 1973.

*Primary Examiner*—Paul Lieberman
*Assistant Examiner*—John R. Hardee
*Attorney, Agent, or Firm*—Millen, White, Zelano & Branigan, P.C.

[57] ABSTRACT

The invention relates to compounds of formula:

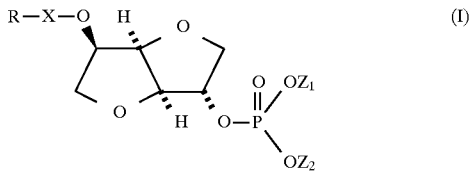

(I)

or

-continued

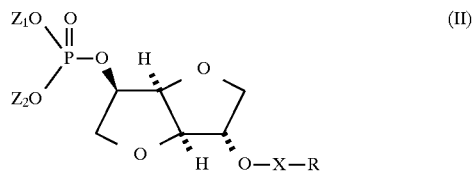

(II)

The invention also relates to a process for the preparation of the said compounds, which consists in:

a) reacting dianhydro-1,4:3,6-D-glucitol with a compound of formula RCOOR' or $RCH_2Y$ in the presence of a catalyst to form compounds of formula:

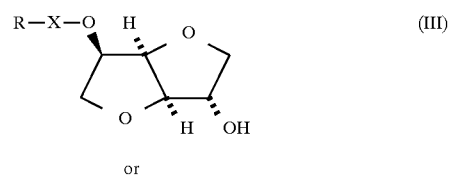

(III)

or

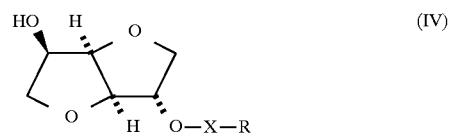

(IV)

in which:

Y represents a halogen or an alkyl or arylsulfonic radical,

R' represents a hydrogen atom or an alkyl radical having from 1 to 6 carbon atoms, R represents a saturated or unsaturated linear or branched alkyl radical containing from 5 to 21 carbon atoms, x represents CO or $CH_2$;

b) reacting the product of step a) with phosphorus oxychloride, a base and an anhydrous solvent, to form the compounds of formula (I) and/or (II), and optionally in separating them.

The compounds which form the subject of the invention can be used in the field of surfactants, in particular for the preparation of cosmetic or hair compositions.

17 Claims, No Drawings

PHOSPHORIC ESTERS OF ALKYL OR ACYL DIANHYDRO-1,4:3,6-D-GLUCITOL, PREPARATION PROCESS AND USES THEREOF

BACKGROUND OF THE INVENTION

The invention relates to novel phosphoric esters of dianhydro-1,4:3,6-D-glucitol (or isosorbide), to a process for their preparation and to their applications. More precisely, the invention relates to the phosphoric esters of alkyl or acyl isosorbide having surfactant properties, to a process for their preparation and to their use, in particular for preparing cosmetic or detergent compositions.

It is well known that grafts of in particular alkyl or acyl substituents onto glucides leads to compounds having often specific surfactant properties and which are, in addition, biodegradable.

Glucides of the dianhydro-1,4:3,6-D-glucitol series have in particular formed the subject of many studies.

Thus, it has been proposed to prepare alkyloyldian-hydro-1,4:3,6-D-glucitol by selective chemical esterification in position 2 or 5 [see for example Cekovic Z. and Tokiec Z., Synthesis, pp. 610-612 (1989); Le Lem G. et al., Bull. Soc. Chim. Fr., No. 3, pp. 567–570 (1988); Abenhaïm D. et al., Carbohyd. Res., 261, pp. 255–266 (1994)]. These compounds are used in particular as intermediates in the synthesis of vasodilators (Monis-2 and Monis-5).

Mukesh D. et al. [Biotech. Lett. Vol. 15, No. 2, pp. 1243–1246 (1993)] describe a mixture of dianhydro-1,4:3,6-D-glucitol monooleates obtained by catalytic esterification using an immobilized lipase.

Zarif L. et al. [J. Fluor. Chem. Vol. 44, pp. 73–85 (1989)] propose to prepare dianhydro-1,4:3,6-D-glucitol perfluoroalkyl monoesters which can be used in the biomedical field (blood substitutes).

Jazinski W. and Ropusynski S. [CA 79: 146 767 h; CA 80: 61 387e; CA 80: 146 h] propose a mixture comprising the 2-(trisodium pyrophosphate), 2-(disodium pyrophosphate) and 2-phosphate derivatives of 5-acyldianhydro-1,4:3,6-D-glucitol, in which the acyl radical represents an oleyl, stearyl or lauryl radical.

Lastly, SAHEKI et al. [JAOCS, Vol. 63 No. 7, pp. 927–930 (1986)] propose 2-alkyloyldianhydro-1,4:3,6-D-glucitol 5-sulphates in which the alkyloyl radical contains from 8 to 16 carbon atoms. Such compounds can be used as surfactants.

In the field of surfactants, there is a great need to study compounds whose resistance to hydrolysis and compatibility with the skin and the mucous membranes are improved.

SUMMARY OF THE INVENTION

The subject of the present invention is thus novel phosphoric esters of formula:

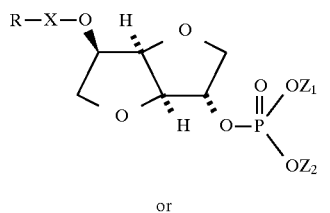

(I)

or

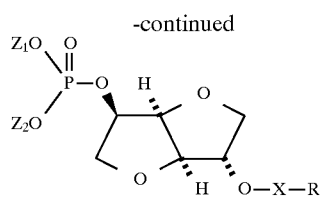

(II)

in which:
R represents a saturated or unsaturated linear or branched alkyl radical containing from 5 to 21 carbon atoms,
X represents CO or $CH_2$,
$Z_1$ and $Z_2$, which are identical or different, represent a hydrogen atom, an alkali metal, an alkaline-earth metal or a quaternary ammonium of formula:

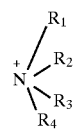

in which $R_1$, $R_2$, $R_3$ and $R_4$, which are identical or different, represent a hydrogen atom, an alkyl or hydroxyalkyl radical containing from 1 to 6 carbon atoms or a basic amino acid residue.

The subject of the invention is also a process for the preparation of the abovementioned compounds of formula (I) or (II), which consists of:
a) reacting dianhydro-1,4:3,6-D-glucitol with a compound of formula RCOOR' or $RCH_2Y$ in the presence of a catalyst to form the compounds of formulae:

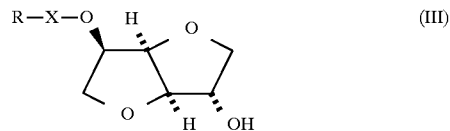

(III)

and

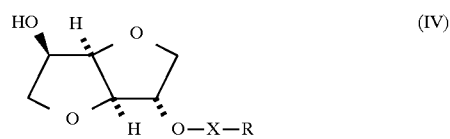

(IV)

in which:
Y represents a halogen or an alkyl or arylsulphonic radical,
R' represents a hydrogen atom or an alkyl radical having from 1 to 6 carbon atoms,
R and X have the meaning given above, optionally in separating the said compounds in (III) and in (IV), and
b) in reacting the product of step a) with phosphorus oxychloride, a base and an anhydrous solvent.

Another subject of the invention relates to the application of the abovementioned compounds of formulae (I) and (II) as surfactants.

Another subject of the present invention relates again to the particular cosmetic or detergent compositions comprising the abovementioned compounds.

The process for preparing the compounds according to the invention is described in detail in the following text:
STEP A: PREPARATION OF THE COMPOUNDS OF FORMULAE (III) AND (IV)
1. Preparation of the esters (X=CO)
The esters of formulae (III) and (IV) are obtained by reacting dianhydro-1,4:3,6-D-glucitol with a fatty acid or a fatty acid ester of formula RCOOR' in the presence of a catalyst.

The fatty acid ester is chosen from fatty acids with a saturated or unsaturated linear or branched chain containing from 6 to 22 carbon atoms, preferably 7 to 18 carbon atoms.

The fatty acid ester is chosen from the esters of the abovementioned fatty acids in which the ester group comprises from 1 to 6 and preferably 1 to 2 carbon atoms.

The catalyst varies depending on the nature of the compound of formula RCOOR'.

When a fatty acid is used, the catalyst consists of an acid. By way of illustration, mention may be made of hydrochloric acid, sulfuric acid, alkylsulfuric acids, for example decylsulfuric or laurylsulfuric acid, aryl sulfonic acids, for example benzenesulfonic, para-toluenesulfonic or camphorsulfonic acid, alkylsulfonic acids, for example methanesulfonic, decylsulfonic, laurylsulfonic or sulfosuccinic acid or an alkyl sulfosuccinate such as decyl or lauryl sulfosuccinate, perhalohydric acids, for example perchloric acid, hypophosphorous acid or mixtures of these acids. Sulfuric acid, an alkylsulfuric acid, methanesulfonic acid, succinic acid or an alkyl sulfosuccinate, hypophosphorous acid or mixtures of these acids are preferably used.

When a fatty acid ester is used, the catalyst is a base. By way of illustration of such a base, mention may be made of metal alkoxides such as methoxides or ethoxides of an alkali metal such as sodium or potassium, carbonates and bicarbonates, for example of an alkali metal such as sodium or potassium, compounds of formula M(OH). in which M is an alkali metal or an alkaline-earth metal and x is the valency of the metal, basic aluminas, quaternary ammonium hydroxides of formula:

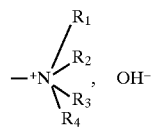

in which $R_1$, $R_2$, $R_3$ and $R_4$, which are identical or different, represent an alkyl or alkylaryl radical containing from 1 to 18 carbon atoms, or mixtures of these bases.

Advantageously, a phase transfer catalyst chosen from the known catalysts, such as, for example, tetrabutylammonium halides (in particular bromide) or methyltrioctylammonium halides (in particular chloride) may be added to the abovementioned base.

The abovementioned catalyst is generally used in a proportion of from 0.1 to 20%, and preferably 1 to 5%, by weight relative to the starting dianhydro-1,4:3,6-D-glucitol.

The abovementioned esters may be prepared in the presence of a solvent, either from the fatty acid or from the ester of this acid. By way of example, mention may be made of alkanes, oxide ethers such as tetrahydrofuran, dioxane or diethylene glycol dimethyl ether, halohydrocarbons such as dichloromethane, chloroform or dichloroethane, solvents of the amide type such as N-methylformamide, N,N-dimethylformamide, N,N-dimethylacetamide or N-methyl-2-pyrrolidone, nitrites such as acetonitrile, suphoxides such as dimethyl sulphoxide, aromatic solvents such as toluene or xylene, and mixtures of these solvents.

In the preparation of the esters according to the invention, from 0.1 to 20 molar equivalents, and preferably 0.5 to 10 equivalents, of dianhydro-1,4:3,6-D-glucitol, from $0.5 \times 10^{-3}$ to 2 molar equivalents of acidic or basic catalyst, and preferably $1 \times 10^{-3}$ to $1 \times 10^{-1}$ equivalent (acidic catalyst) or $1 \times 10^{-2}$ to 1 equivalent (basic catalyst) and from 0 to 20 equivalents by weight, and preferably 0 to 10 equivalents, of solvent, calculated on the basis of one equivalent by weight of fatty acid or of esters of the said starting acid, are generally used.

The reaction is generally carried out at a temperature of between 25° and 200° C., and preferably 70 to 180° C., for a period which can range from 1 minute to 48 hours, and preferably 2 minutes to 24 hours, and at a pressure of between 0.013 and 101.325 kPa.

Advantageously, in particular in order to decrease the time, the reaction is carried out under microwave irradiation.

After the reaction, the reaction medium is generally filtered so as to remove the catalyst. The filtrate thus obtained contains the esters of formulae (III) and (IV); the compounds may optionally be separated out, for example by chromatography on a column of silica or by precipitation and/or recrystallization from a solvent chosen from the abovementioned solvents and solvents of the ester family such as ethyl, propyl or butyl acetate.

2. Preparation of the ethers ($X=CH_2$

The ethers of formulae (III) and (IV) are prepared by reacting dianhydro-1,4:3,6-D-glucitol with a compound of formula $RCH_2Y$ in the presence of a catalyst.

The compound of formula $RCH_2Y$ in which R and Y are defined as above is preferably chosen from compounds containing a chlorine atom or a $C_{1-7}$-sulfonyl radical such as methanesulfonyl or para-toluenesulfonyl.

The catalyst is chosen from the bases defined above, the alkali metals and the hydrides of these metals. Preferably, sodium, potassium, sodium hydride or lithium hydride is used.

Advantageously, a phase transfer catalyst chosen from quaternary ammonium salts such as tetraalkylammonium or tetraarylalkylammonium halides, for example tetrabutylammonium chloride or bromide, and ammonium hydrogen sulfates, for example methyltrioctylammonium, benzyltrimethylammonium or benzyltriethylammonium hydrogen sulfate may be added to the abovementioned catalyst.

This catalyst may also contain salts such as halides or perchlorates of an alkali metal, for example of rubidium or caesium.

The reaction may also be carried out in the presence of one of the abovementioned solvents, water and miscible or immiscible mixtures of these compounds.

In the preparation of the ethers according to the invention, from 1 to 20 molar equivalents, and preferably 1 to 5 equivalents, of dianhydro-1,4:3,6-D-glucitol, from 1 to 20 molar equivalents, and preferably 1 to 5 equivalents, of catalyst and from 0 to 20 equivalents by weight, and preferably 0 to 10 equivalents, of solvent, calculated on the basis of one equivalent by weight of the compound of formula $RCH_2Y$, are generally used.

The reaction is generally carried out at a temperature of between 0° and 200° C., and preferably 25° to 160° C., for a period which may range from 1 minute to 48 hours, and preferably 2 minutes to 24 hours.

Advantageously, in particular in order to decrease the time, the reaction is carried out under microwave irradiation.

After the reaction, the ethers of formulae (III) and (IV) are recovered from the reaction medium. These ethers may optionally be separated, for example by chromatography on a column of silica.

STEP B: PREPARATION OF THE COMPOUNDS OF FORMULE (I) AND (II)

The reaction product of step a) is reacted with phosphorus oxychloride, a base and an anhydrous solvent.

The reaction product of step a) generally consists of the compound of formula (III) or (IV) in the form either of an ester ($X=CO$) or of an ether ($X=CH_2$).

However, these compounds can be used in the form of a mixture of esters or ethers or esters and ether.

The phosphorus oxychloride is generally predistilled.

The base is chosen from pyridine, N, N-dimethyl- or -diethylamino-4-pyridine and tertiary amines such as N-methyl- or N-ethylmorpholine.

The anhydrous solvent is generally chosen from the solvents mentioned above. Preferably, chlorinated solvents such as chloroform, dichloromethane or dichloroethane and oxide-ethers such as tetrahydrofuran, dioxane, ethylene glycol dimethyl ether or diethylene glycol dimethyl ether are used.

In carrying out step b) of the process according to the invention, from 1 to 5 molar equivalents, and preferably 1 to 2 equivalents, of phosphorus oxychloride, from 1 to 5 molar equivalents, and preferably 1 to 5 equivalents, of the base and from 1 to 50 equivalents by weight, and preferably 1 to 20 equivalents, of the solvent, calculated on the basis of one equivalent by weight of the starting compound of formula (III) and/or (IV), are generally used.

The reaction is generally carried out at a temperature of between −20° and +60° C., and preferably −10° to +40° C., for a period ranging from 1 hour to 7 days, and preferably 1 hour to 48 hours.

Advantageously, the reaction is carried out under an inert, anhydrous atmosphere, for example by bubbling argon and nitrogen through.

After the reaction, the chloride corresponding to the base used is removed from the reaction medium by filtration. The filtrate, to which a solvent as defined above, and preferably an alkane (for example hexane or heptane), is added, is evaporated off. The evaporation residue, to which 1 to 20 equivalents by weight of ice-water are added, is maintained at a temperature of between 0° and 40° C., preferably 10° and 30° C., for 30 minutes to 5 hours, preferably 1 to 2 hours, with vigorous stirring.

The compound I or II present in the aqueous phase thus obtained may be recovered in several ways, for example:
  by concentration of the said phase, in particular under vacuum and at a temperature in the region of 60° C.,
  by extraction of the said phase with at least one organic solvent specially for this purpose and concentration of the organic phase(s),
  by basification of the said phase and addition of at least one solvent which is capable of causing the abovementioned compound to precipitate out, it then being possible for this compound advantageously to be recovered by filtration, for example through a sinter funnel.

The compound of formula (I) or (II) may optionally undergo an additional step of purification, for example by exclusion chromatography on a column of gel such as cyano-econosil prepCN (90 Å; 15–35 µm; Alltech) or by ion-exchange chromatography on a strong cationic resin such as Amberlite IR 120H$^+$, or by recrystallization.

The phosphoric esters of formulae (I) and (II) have surfactant properties, in particular solubilizing, emulsifying, foam-forming, wetting and dispersing properties. In addition, the compounds according to the invention have the property of not being aggressive towards the skin and the mucous membranes, thereby making them particularly suitable for the preparation of compositions intended for hygiene, such as shampoos and cosmetic or hair compositions, for example ointments, creams, beauty milks, etc.

On account of their foaming power and their capacity to soften the skin, the compounds according to the invention may also be used in bath compositions (foaming baths) or shower compositions (shower gel), as well as in soaps in particular of syndet ("Synthetic Detergent") type. Suitable excipients and other agents for such compositions are well known in the art, e.g., for cleansing skin, hair or mucous membranes, and include, e.g., surfactants, for example, of the neutral or amphoteric type such as polyalkylglycosides and alkylamidopropyl betaines, respectively.

The compounds according to the invention may also be used as antistatic agents for the treatment of textiles, wetting agents and detergents for special uses, wetting agents for the treatment of textiles and leather, and emulsifiers in fields such as petroleum research, the treatment of metals and suspension polymerization. Suitable excipients and co-agents for such compositions are well known in the art and include, e.g., a solvent (preferably organic) or an aerosol for antistatic treatment of textiles; and a solvent (preferably organic) or an aerosol for treatment of metals, respectively.

For the use in polymerization reactions, the compounds according to the invention act as adjusting agents for the size of the polymer particles.

Suitable amounts of the compounds according to the invention for the various uses include, but are not limited to, e.g., for hygiene compositions: 1–30% (preferably 5–20%); and for other compositions: less than 15% (preferably 0.5–5%), both expressed on a w/w basis.

The examples which follow allow the invention to be illustrated. In the examples, the following analysis methods are used:
  the Rf is measured by thin-layer chromatography on silica (thickness of the film: 200 µm; particle size: 5–10 µm). The migration solvent is a 50/50 (v/v) ethyl acetate/hexane mixture. The migration spots are detected by spraying with sulfuric acid at a concentration of 50% by volume in water and heating at 120° C. for 2 minutes:
  nuclear magnetic resonance (NMR):
    $^1$H: performed at 250 MHz in the presence of CDCl$_3$. The chemical shifts are expressed in ppm and the coupling constants (J) in Hz.
    $^{13}$C performed at 75 MHz in the presence of CDCl$_3$ (Examples 1–4, 7–8) or D$_2$O (Example 5). The chemical shifts are expressed in ppm and the coupling constants (J) in Hz.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 96.03813, filed Mar. 27, 1996, are hereby incorporated by reference.

EXAMPLES

Example 1

Preparation of the compounds of formulae (III-a) and (IV-a): X=CO and R=C$_{11}$H$_{23}$.

1.52 g (10.4 mmol) of dianhydro-1,4:3,6-D-glucitol (Roquette Frères), 4.46 g (20.8 mmol) of methyl dodecanoate (Fina Chemicals), 0.94 g (6.8 mmol) of potassium carbonate, 0.1 g (0.31 mmol) of tetrabutylammonium bromide and 2 ml of dimethylformamide are mixed together.

The mixture obtained is subjected to a microwave irradiation of 20 watts for 15 minutes with stirring.

After cooling, the cake obtained is solubilized in 20 ml of ethyl acetate and the solution is concentrated under vacuum in a rotary evaporator (60° C.; 2.4 kPa and then 0.1 kPa).

The solution thus concentrated is chromatographed on a column (φ=2.5 cm; length =15 cm) filled with silica (200–300 mesh, ASTM) eluted with heptane and then with a 95/5 (v/v) heptane/ethyl acetate mixture.

0.586 g of 2-O-dodecanoyldianhydro-1,4:3,6-D-glucitol (IV-a) and 1.67 g of 5-O-dodecanoyldianhydro-1,4:3,6-D-glucitol (III-a) are successively eluted, i.e., yields, calculated on the basis of the starting dianhydro-1,4:3,6-D-glucitol, equal to 17.1% and 48.9%, respectively.

Example 2

Preparation of the compounds of formulae (III-a) and (IV-a): X=CO and R=$C_{11}H_{23}$.

A mixture comprising 150 g (748.8 mmol) of dodecanoic acid (ref. 15, 378-8; Aldrich), 547 g (3743 mmol) of dianhydro-1,4:3,6-D-glucitol (Roquette Frères) and 1.75 g of an equimolar mixture of methanesulfonic acid and hypophosphorous acid is heated at 160° C. for 8 hours under a nitrogen atmosphere.

The reaction medium obtained (678 g) is dissolved in one liter of heptane and placed at 4° C. for 24 hours. A precipitate forms which is recovered by filtration and partially dissolved in ethyl acetate (4×200 ml). The organic phases are combined, washed with water (2×100 ml), dried (magnesium sulphate), filtered (No. 3 sinter funnel) and concentrated in a rotary evaporator. The evaporation residue is recrystallized from pentane.

The recrystallized compound (104 g) consists of 2-O-dodecanoyldianhydro-1,4:3,6-D-glucitol (IV-a), i.e. a yield, calculated on the basis of the starting dodecanoic acid, equal to 42%. The organic phase (heptane) is concentrated in a rotary evaporator and the residue obtained is precipitated from pentane. After filtration, the organic phase is washed with water, dried (magnesium sulfate), filtered and concentrated in a rotary evaporator. 53 g of 5-O-dodecanoyldianhydro-1,4:3,6-D-glucitol (III-a) are recovered, i.e. a yield, calculated on the basis of the starting dodecanoic acid, equal to 21.6%.

The characteristics of compounds (III-a) and (IV-a) are presented below.

Melting point compound (IV-a): 78° C. (pentane)

compound (III-a): oil

Rf on thin-layer chromatography compound (IV-a): 0.5 compound (III-a): 0.4

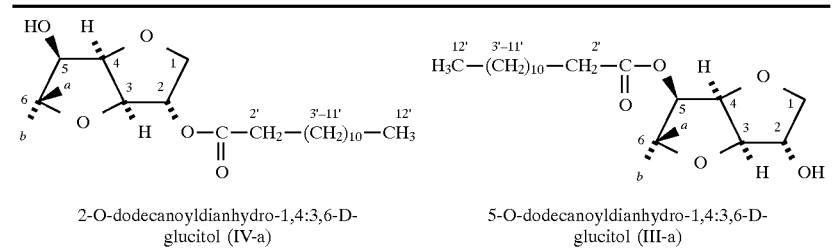

| 2-O-dodecanoyldianhydro-1,4:3,6-D-glucitol (IV-a) | | 5-O-dodecanoyldianhydro-1,4:3,6-D-glucitol (III-a) | |
|---|---|---|---|
| $^1$H NMR | | | |
| H2: 5.25–5.20; bs | | H5: 5.20–5.10; dxdxd | |
| H4: 4.65–4.55; t | | H4: 4.90–4.80; t | |
| H3: 4.50–4.40; bd | | (J 4.5 = 5) | |
| (J 3.2 < 1, J 3.4 = 5) | | H3: 4.43–4.37; bd | |
| H5: 4.35–4.20; dxdxd | | (J 3.2 < 1, J 3.4 = 5) | |
| (J 4.5–5) | | H2: 4.35–4.30; bs | |
| H1b, 1a: 4.00; d | | (J 2.1 < 1) | |
| (J 1a, 1b = 2.8, J 1a, 2 < 1) | | H1a, 1b, 6b: 3.95–3.80; m | |
| H6b: 3.95–3.80; dxd | | H6a: 3.80–3.70 | |
| H6a: 3.60–3.50; dxd | | (J 6a, 6b = 10, J6a, 5 = 6) | |
| (J 6a, 6b = 10, J 6a, 5 = 6 | | OH-2: 2.90–2.70; m | |
| OH-5: 2.75–2.60; m | | $CH_2$-2': 2.40–2.30; t | |
| $CH_2$-2': 2.40–2.25; t | | $CH_2$-3': 1.70–1.55; m | |
| $CH_2$-3': 1.70–1.55; m | | $CH_2$-4'–11': 1.45–1.15 (16H); m | |
| $CH_2$-4'–11': 1.40–1.15; m | | $CH_3$-12': 0..90; m | |
| $CH_3$-12': 0.95–080 | | | |
| $^{13}$C NMR | | | |
| 173.4 | C=O | 172.8 | C=O |
| 88.3 | C3 | 85.8 | C3 |
| 80.4 | C4 | 82.0 | C4 |
| 76.2 | C2 | 78.2 | C2 |
| 75.5 | C1 | 73.7 | C1 |
| 74.0 | C5 | 73.6 | C6 |
| 70.4 | C6 | 72.4 | C5 |
| 34.1–22.7 | $CH_2$-2'–11' | 34.2–22.7 | $CH_2$-2'–11' |
| 14.1 | $CH_3$-12' | 14.1 | $CH_3$-12' |

EXAMPLE 3

Preparation of the compounds of formulae (III-b) and (IV-b): X=$CH_2$ and R=$C_{11}H_{23}$. 10 g (68 mmol) of dianhydro-1,4:3,6-D-glucitol (Roquette Frères) are dissolved in a mixture consisting of 35 ml of dimethyl sulfoxide and 10 ml of deionized water. 5.8 g (89 mmol) of potassium hydroxide are added to the abovementioned solution and the mixture obtained is placed in an oil bath at 90° C. The mixture is stirred for 20 minutes and 13 g (52 mmol) of bromododecane (B6, 551-1; Aldrich) are added dropwise.

After 24 hours, the reaction mixture is filtered through 10 ml of silica (230–400 mesh, ASTM). The filtrate is concentrated in a rotary evaporator (60° C.; 2.4 kPa and then 0.01 kPa) and the residue obtained, taken up in 100 ml of a 50/50 (v/v) water/ethyl acetate mixture, is stirred at 400 rpm for 5 minutes. The organic phase is recovered, washed with water (2×20 ml), dried (magnesium sulfate) and concentrated in a rotary evaporator (50° C.; 2.4 kPa).

The residue obtained is adsorbed onto 5 ml of silica (230–400 mesh, ASTM) and chromatographed on a column (φ=5.6 cm; length=25 cm) filled with the abovementioned silica and provided with a system of detection by differential refractometry. Elution using a heptane/ethyl acetate gradient (100/0 to 50/50 (v/v) over 30 minutes) allows 0.95 g of 2-O-dodecyldianhydro-1,4:3,6-D-glucitol (IV-b) and 2.3 g of 5-O-dodecyldianhydro-1,4:3,6-D-glucitol (III-b) to be successively recovered, i.e. yields, calculated on the basis of the starting bromododecane, equal to 6.1 and 14.0% respectively.

EXAMPLE 4

Preparation of compounds of formulae (III-b) and (IV-b): $X=CH_2$ and $R=C_{11}H_{23}$.

43.9 g (0.3 mol) of dianhydro-1,4:3,6-D-glucitol (Roquette Frères) are introduced into a 250 ml round-bottomed flask fitted with a mechanical stirrer system, a condenser and a guard tube ($CaCl_2$). The flask is heated to 90° C. and 1 g (0.12 mol) of lithium hydride is added portionwise. After one hour, 24.9 g (0.1 mol) of bromododecane (20,104-9; Aldrich) are added dropwise, the mixture is stirred for 3 hours at 140° C. and is cooled to 60° C. The mixture is transferred into a one liter round-bottomed flask and 100 ml of deionized water and 200 ml of ethyl acetate are added cautiously. The mixture is stirred for 5 minutes and the organic phase is recovered, washed with water (2×50 ml), dried (magnesium sulfate) and concentrated in a rotary evaporator. 21.4 g of a brown oil are obtained, which product is chromatographed on a column (φ=5.8 cm; length= 25 cm) filled with silica (230–400 mesh, ASTM) provided with a system of detection by differential refractometry. The column is eluted using a 50/50 (v/v) ethyl acetate/hexane mixture at a rate of 40 ml/min. −3 g of 2-O-dodecyldianhydro-1,4:3,6-D-glucitol (IV-b), 5 g of 5-O-dodecyldianhydro-1,4:3,6-D-glucitol (III-b) and 1.6 g of a mixture of the abovementioned two compounds (IV-b and III-b) are successively recovered, i.e. yields, calculated on the basis of the starting bromododecane, equal to 9.5, 16 and 5% respectively.

The characteristics of compounds (IV-b) and (III-b) are presented below.

Melting point compound (IV-b): oil compound (III-b): 55° C. (pentane)

Rf compound (IV-b): 0.60 (ethyl acetate/heptane) 0.45 (ethyl acetate/hexane)

compound (III-b): 0.40 (ethyl acetate/heptane) 0.26 (ethyl acetate/hexane)

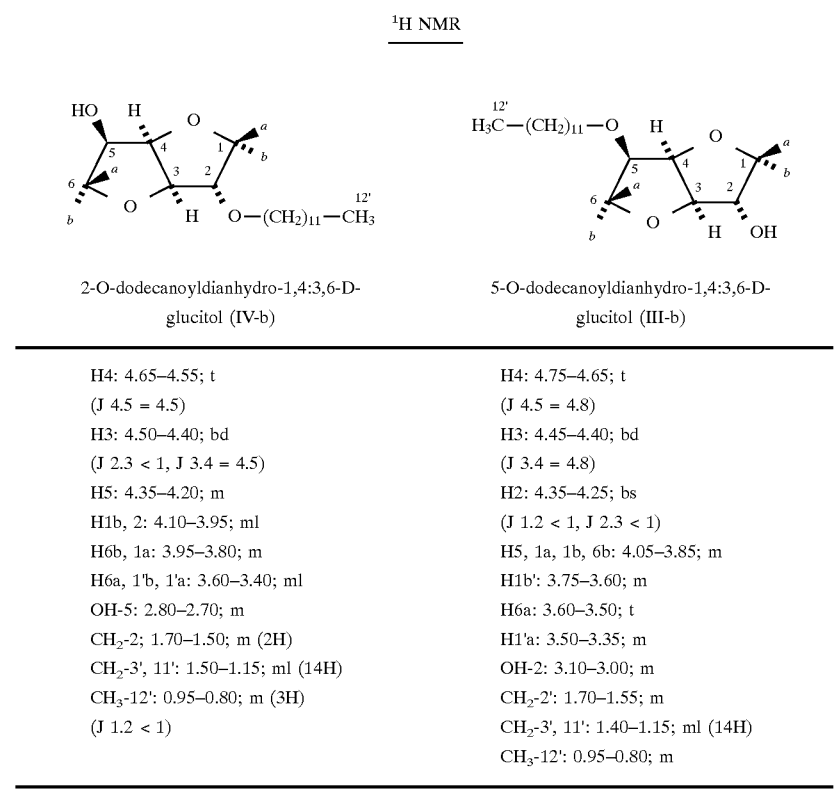

¹H NMR

| 2-O-dodecanoyldianhydro-1,4:3,6-D-glucitol (IV-b) | 5-O-dodecanoyldianhydro-1,4:3,6-D-glucitol (III-b) |
|---|---|
| H4: 4.65–4.55; t | H4: 4.75–4.65; t |
| (J 4.5 = 4.5) | (J 4.5 = 4.8) |
| H3: 4.50–4.40; bd | H3: 4.45–4.40; bd |
| (J 2.3 < 1, J 3.4 = 4.5) | (J 3.4 = 4.8) |
| H5: 4.35–4.20; m | H2: 4.35–4.25; bs |
| H1b, 2: 4.10–3.95; ml | (J 1.2 < 1, J 2.3 < 1) |
| H6b, 1a: 3.95–3.80; m | H5, 1a, 1b, 6b: 4.05–3.85; m |
| H6a, 1'b, 1'a: 3.60–3.40; ml | H1b': 3.75–3.60; m |
| OH-5: 2.80–2.70; m | H6a: 3.60–3.50; t |
| $CH_2$-2; 1.70–1.50; m (2H) | H1'a: 3.50–3.35; m |
| $CH_2$-3', 11': 1.50–1.15; ml (14H) | OH-2: 3.10–3.00; m |
| $CH_3$-12': 0.95–0.80; m (3H) | $CH_2$-2': 1.70–1.55; m |
| (J 1.2 < 1) | $CH_2$-3', 11': 1.40–1.15; ml (14H) |
| | $CH_3$-12': 0.95–0.80; m |

-continued

$^{13}$C NMR

| 2-O-dodecanoyldianhydro-1,4:3,6-D-glucitol (IV-a) | | 5-O-dodecanoyldianhydro-1,4:3,6-D-glucitol (III-a) | |
|---|---|---|---|
| 86.1 | C3 | 88.4 | C3 |
| 84.2 | C2 | 80.4 | C5 |
| 81.8 | C4 | 80.1 | C4 |
| 73.6 | C1, C6 | 76.7 | C2 |
| 72.3 | C5 | 75.9 | C1 |
| 70.0 | C1' | 71.1 | C1' |
| 32.0–22.7 | C2', C11' | 70.1 | C6 |
| 14.1 | C12', CH$_3$ | 31.9–22.7 | CH$_2$-2',11' |
|  |  | 14.1 | CH$_3$-12' |

EXAMPLE 5

Preparation of compound (II-a): X=CO; R=C$_{11}$H$_{23}$ and Z$_1$=Z$_2$=H.

1 g (3.04 mmol) of 2O-dodecanoyldianhydro-1,4:3,6-D-glucitol (compound IV-a) of Example 1 is dissolved in 10 ml distilled and anhydrous dichloromethane (washed with water, dried with CaCl$_2$, distilled over P$_2$O$_5$). The solution is placed at 0° C. under an argon atmosphere and 0.385 g (3.34 mmol) of distilled N-ethylmorpholine is added, along with dropwise addition of 0.469 g (3.05 mmol) of distilled phosphorus oxychloride. The mixture obtained turns yellow.

This mixture, maintained at 20° C. with stirring for 4 hours, was concentrated in a rotary evaporator. The evaporation residue is suspended in 20 ml of heptane at 0° C., stirred for 10 minutes and filtered through a sinter funnel (porosity 3).

The filtrate thus recovered, maintained at 0° C., is hydrolysed with 20 ml of an aqueous buffer solution (acetic acid/sodium acetate; pH=4.75).

After stirring for one hour at 20° C., the mixture is concentrated in a rotary evaporator (60° C.; 2.4 kPa).

The evaporation residue is purified by chromatography on a column of Cyanoeconosil Prep-CN (Alltech; pore diameter: 90 Å; particle size: 15–35 µm) eluted using an ethyl acetate/hexane gradient (0/100 to 50/50 (v/v)) and an ethyl acetate/ethanol gradient (90/10 to 0/100 (v/v)).

After concentration of the organic phases in a rotary evaporator, a yellowish pasty foam is recovered containing 0.281 mg of 2-O-dodecanoyldianhydro-1,4:3,6-D-glucitol 5-phosphate (II-a), i.e. a yield, calculated on the basis of the starting compound (IV-a), equal to 22%.

The characteristics of compound (II-a) are presented below.

$^1$H NMR

2-O-dodecanoyldianhydro-1,4:3,6-D-glucitol-5-phosphate (II-a)

| O‖O—P—OH\|OH |  8.30–8.00; m |
|---|---|
| H2 | 5.20–5.15; m |
| H4,5 | 4.90–4.70; m |
| H3 | 4.55–4.45; m |
| H1a, 1b, 6b | 4.15–3.85; m |
| H6a | 3.90–3.70; m |
| CH$_2$-2' | 2.40–2.20; t |
| CH$_2$-3' | 1.70–1.50; m |
| CH$_2$-4'–11' | 1.50–1.00; m |
| CH$_3$-12' | 1.70–0.75; m |

$^{31}$P NMR: reference H$_3$PO$_4$
Phosphate peak at 0 ppm.
$^{13}$C NMR: potassium salt
CO: 184.57
C$_1$–C$_6$ : 87.07; 81.54; 76.07; 75.05; 74.08; 69.99;
(CH$_2$)$_n$-2'-11': 38.25; 31.94; 29.61; 29.39; 29.31; 26.55; 22.72;
CH$_3$-12': 14.03

EXAMPLE 6

Preparation of compound (I-a): X=CO; R=C$_{11}$H$_{23}$ and Z$_1$=Z$_2$=H.

To a solution of 2.3 g (15 mmol) of freshly distilled phosphorus oxychloride in 40 ml of anhydrous tetrahydrofuran (sodium/benzophenone system), maintained at 0° C.

with stirring for 30 minutes, is added a solution containing 4.75 g (15 mmol) of pyridine in 60 ml of tetrahydrofuran along with dropwise addition of 3.29 g (10 mmol) of 5-O-dode-canoyldianhydro-1,4:3,6-D-glucitol (compound III-a according to Example 1) dissolved in 60 ml of tetrahydrofuran. After 1 hour at 0° C. and 18 hours at 20° C., a precipitate of pyridinium chloride forms, which is removed by filtration through a sinter funnel (porosity 3).

The filtrate obtained, to which 80 ml of a water/crushed ice mixture is added, is stirred (800 rpm; 1 hour). After adding 100 ml of a 2/3 (v/v) chloroform/methanol mixture followed by separation of the phases after settling has taken place, the whitish organic phase is recovered and treated with 50% by weight of potassium hydroxide solution until the pH is equal to 9.5. The brown emulsion thus formed is concentrated in a rotary evaporator in the presence of ethanol and then toluene.

The evaporation residue, dissolved in water, is chromatographed on a column filled with a strong cationic resin (Amberlite IR 120 H$^+$). After concentration under vacuum (40° C.; 13.3 Pa) of the solution obtained from the column, 2 g of 5-O-dode-canoyldianhydro-1,4:3,6-D-glucitol 2-phosphate (I-a) are recovered.

EXAMPLE 7

Preparation of compound (I-b): $X=CH_2$, $R=C_{11}H_{23}$ and $Z_1=Z_2=H$.

The process is performed under the conditions of Example 5 in the presence of 5O-dodecyldianhydro-1,4:3,6-D-glucitol (compound III-b according to Example 4), the hydrolysis being carried out using 10 ml of water. 0.37 g (yield: 32%) of 5O-dodecyldianhydro-1,4:3,6-D-glucitol 2-phosphate (I-b) is recovered.

The characteristics of compound (I-b) are presented below.

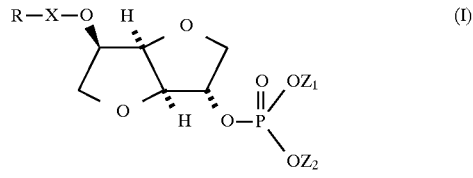

| $^1$H | | $^{13}$C | |
|---|---|---|---|
| H2: 4.84–4.76 | | C3: | 86.37 |
| H4: 4.76–4.71 | | C2: | 80.92 |
| H3: 4.71–4.65 | | C4: | 80.28 |
| H1b: 4.20–4.10 | | C5: | 80.00 |
| H5, 1a, 6b: 4.07–3.90 | | C1: | 74.17 |
| H1'b 3.70–3.60 | | C1': | 71.17 |
| H6a: 3.60–3.52 | | C6: | 70.08 |
| H1'a: 3.48–3.37 | | | 31.94–29.67 |
| | | C2'–C11': | 29.53–29.38 |
| | | | 26.01–22.69 |
| | | C12': | 14.11 |

EXAMPLE 8

Preparation of compound (II-b): $X=CH_2$, $R=C_{11}H_{23}$ and $Z_1=Z_2=H$.

The process is performed under the conditions of Example 6 in the presence of 2-O-dodecyldianhydro-1,4:3,6-D-glucitol (compound IV-b) according to Example 4.

1.52 g (yield: 40%) of 2-O-dodecyldianhydro-1,4:3,6-D-glucitol 5-phosphate (II-b) are recovered.

The characteristics of compound (II-b) are presented below.

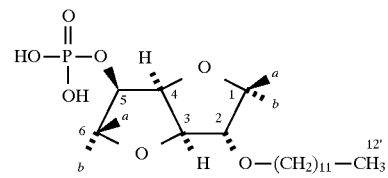

| $^1$H | $^{13}$C |
|---|---|
| H4.5: 5.00–4.70; m | C3: 85.7 |
| H3: 4.50–4.40; dl | C2: 84.0 |
| H1a, 1b, 6b, 2: 4.10–3.80; m | C4: 81.1 |
| H6a: 3.80; 3.60; m | C5: 76.1 |
| H1'a, 1'b: 3.50–3.30; m | C1: 73.7 |
| CH$_2$-2': 1.70–1.55; m | C6: 70.3 |
| CH$_2$-3', 11': 1.45–1.15 (14H) m | CH$_2$-1': 70.1 |
| CH$_3$-12': 0.95–0.80; m | CH$_2$-2',11': 32.0–22.8 |
| | CH$_3$-12': 14.2 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound of formula:

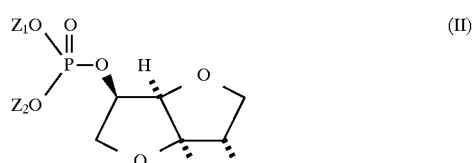

wherein

R is a saturated or unsaturated linear or branched $C_{5-21}$-alkyl radical,

X is -CO- or -CH$_2$-, $Z_1$ and, $Z_2$ are independently, a hydrogen atom, an alkali metal, an alkaline earth metal or a quaternary ammonium of formula:

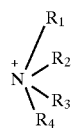

wherein $R_1$, $R_2$, $R_3$ and $R_4$, are, independently, a hydrogen atom, or a C$_{1-6}$-alkyl or -hydroxyalkyl radical or a basic amino acid residue.

2. A compound of claim 1, wherein R is $C_{6-17}$-alkyl.

3. A process for the preparation of a compound of claim 1 comprising:
   a) reacting dianhydro-1,4:3,6-D-glucitol with a compound of formula RCOOR' or RCH$_2$Y in the presence of a catalyst to form a compound of formula:

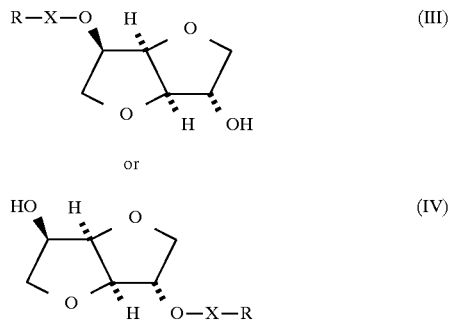

wherein
   Y is halogen or a $C_{1-7}$-alkyl- or arylsulfonic radical,
   R' is hydrogen or a $C_{1-6}$-alkyl radical,
   R is a saturated or unsaturated linear or branched $C_{5-21}$-alkyl radical,
   X is -CO- or -CH$_2$-, and
   b) reacting the product of step a) with phosphorus oxychloride, a base and an anhydrous solvent, to form a compound of formula (I) and/or (II), and optionally, separating said compound of formula (I) and (II).

4. A process of claim 3, wherein the ratio of the number of molar equivalents of dianhydro-1,4:3,6-D-glucitol to the number of molar equivalents of the compound of formula RCOOR' is from 0.1 to 20.

5. A process of claim 3, wherein the ratio of the number of molar equivalents of dianhydro-1,4:3,6-D-glucitol to the number of molar equivalents of the compound of formula RCH$_2$Y is from 1 to 20.

6. A process of claim 3, wherein the base is chosen from pyridine, N,N-dimethyl- or -diethylamino-4-pyridine and tertiary amines.

7. A process of claim 3, wherein the number of molar equivalents of phosphorus oxychloride to the number of molar equivalents of the product of step a) is from 1 to 5.

8. A composition for cleansing skin, hair or mucous membranes, comprising a compound of claim 1 and a topically acceptable cleansing agent.

9. A composition of claim 8, wherein the composition is a shampoo, a cosmetic, or a hair treatment composition.

10. A composition of claim 9, wherein the cosmetic composition is selected from the group consisting of an ointment, cream, beauty milk, foaming bath, shower gel and soap of syndet type.

11. A composition for the antistatic treatment of textiles, comprising a compound of claim 1 and textile-compatible solvent therefor.

12. A composition for treating metal, comprising a compound of claim 1 and a metal-compatible solvent therefor.

13. A composition for emulsifying suspension polymerization reactions, comprising a compound of claim 1 and a polymerization reactant.

14. A method of cleansing skin, hair or mucous membranes, comprising contacting said skin, hair or mucous membranes with a compound of claim 1, and rinsing the compound and associated material cleaned from said skin, hair or mucous membranes therefrom.

15. A method of claim 14, wherein said compound is applied in the form of a shampoo, a cosmetic or a hair treatment.

16. A method of claim 15, wherein the cosmetic composition is selected from the group consisting of an ointment, cream, beauty milk, foaming bath, shower gel and soap of syndet type.

17. A method for the antistatic treatment of textiles, comprising a contacting a textile with of a compound of claim 1.

* * * * *